US008216605B2

(12) United States Patent
Corthesy-Theulaz et al.

(10) Patent No.: US 8,216,605 B2
(45) Date of Patent: Jul. 10, 2012

(54) MODERATING THE EFFECT OF ENDOTOXINS

(75) Inventors: Irène Corthesy-Theulaz, Epalinges (CH); Grigorios Fotopoulos, Wiedlisbach (CH); Gabriela Bergonzelli, Bussigny-Pres-Lausanne (CH)

(73) Assignee: Nestec S.A., Vevey (CH)

( * ) Notice: Subject to any disclaimer, the term of this patent is extended or adjusted under 35 U.S.C. 154(b) by 843 days.

(21) Appl. No.: 10/595,397

(22) PCT Filed: Oct. 12, 2004

(86) PCT No.: PCT/EP2004/011416
§ 371 (c)(1),
(2), (4) Date: Sep. 29, 2006

(87) PCT Pub. No.: WO2005/039606
PCT Pub. Date: May 6, 2005

(65) Prior Publication Data
US 2007/0122453 A1 May 31, 2007

(30) Foreign Application Priority Data
Oct. 13, 2003 (EP) .................................... 03023016

(51) Int. Cl.
*A61K 35/34* (2006.01)
*A61K 36/06* (2006.01)
*A61K 47/00* (2006.01)

(52) U.S. Cl. .................... 424/439; 424/195.16; 424/548
(58) Field of Classification Search .......................... None
See application file for complete search history.

(56) References Cited

U.S. PATENT DOCUMENTS

| 177,534 | A | 5/1876 | Mensman | |
|---|---|---|---|---|
| 4,595,590 | A | 6/1986 | Hublot et al. | |
| 7,198,936 | B2 * | 4/2007 | Silfversparre et al. | 435/252.1 |
| 7,374,753 | B1 * | 5/2008 | Farmer et al. | 424/93.46 |
| 2001/0014322 | A1 * | 8/2001 | Chen et al. | 424/93.45 |
| 2002/0155126 | A1 | 10/2002 | Nakamura et al. | |
| 2004/0022895 | A1 * | 2/2004 | Castro et al. | 426/3 |
| 2005/0244392 | A1 * | 11/2005 | Pei et al. | 424/93.45 |

FOREIGN PATENT DOCUMENTS

| EP | 0 670 117 | 9/1995 |
|---|---|---|
| JP | 61-236727 | 10/1986 |
| JP | 02-207089 | 8/1990 |
| JP | 2001-008636 | 1/2001 |
| JP | 2001-055338 | 2/2001 |
| JP | 2001-218594 | 8/2001 |
| JP | 2002-080351 | 3/2002 |
| JP | 2003-522136 | 7/2003 |
| JP | 2007-508342 | 4/2007 |
| WO | 02/091850 | 11/2002 |

OTHER PUBLICATIONS

Kan Shida et al. "Enterotoxin-binding glycoproteins in a Proteose-Peptone Fraction of Heated Bovine Milk", J Dairy Science 77:930-939, 1994.*
Dubos et al. "Preparation and Properties of Shiga Toxin and Toxoid" From the laboratories of the Rockefeller Institute for medical research, New York and the biological laboratories of E. R. Squibb and sons, New Brunswick, published Apr. 27, 1945.*
Ernest Brody "Biological activities of bovine glycomacropeptide", British Journal of Nutrition (2000), 84, Suppl. 1, S39-S46.*
The Written Opinion of the International Searching Authority, 6 pages.
Arvola, et al., "Early dietary antigens delay the development of gut mucosal barrier in preweaning rats," Pediatric Research, 1992, vol. 32, No. 3, pp. 301-305.
Galeano, et al., "Comparison of two special infant formulas designed for the treatment of protracted diarrhea," Journal of Pediatric Gastroenterology and Nutrition, 1988, vol. 7, No. 1, pp. 76-83.
Sack, et al., Hydrolyzed lactalbumin-based oral rehydration solution for acute diarrhoea in infants, Acta Paediatrica, 1994, vol. 83, No. 8, pp. 819-824.
Japanese Office Action for Japanese Application No. P2006-534666 mailed Feb. 1, 2011.

* cited by examiner

*Primary Examiner* — Michael G Hartley
*Assistant Examiner* — Nabila Ebrahim
(74) *Attorney, Agent, or Firm* — K&L Gates LLP

(57) ABSTRACT

The present invention relates to the use of an oral composition comprising meat extract and peptones, separately or in combination, in the manufacture of an oral composition to treat the effects of infection by pathogenic bacteria such as *Clostridium difficile*. Such effects may include the failure of the integrity of the gut epithelial cells and diarrhoea as well as other COX-2 mediated effects.

9 Claims, No Drawings

MODERATING THE EFFECT OF ENDOTOXINS

FIELD OF THE INVENTION

The present invention relates to a nutritional approach for moderating the effect of enterotoxins resulting from infection by pathogens.

BACKGROUND OF THE INVENTION

Human and animal gastrointestinal tract is at risk to develop various disorders, including these caused by aging, viruses, bacteria and/or their toxins or by physical and chemical abuses, among others.

There are several factors or therapies, which are capable of alleviating the symptoms of the various gastrointestinal disorders. Among others the indigenous flora, known as microbiota, plays an important role in modulating the intestinal environment. The non-pathogenic micro-organisms residing in the gut, known as probiotics, together with the prebiotic molecules, released from the micro-organisms or taken with the diet as food ingredients, present potential means to prevent or treat gastrointestinal disorders, including *C. difficile* infection.

It has been demonstrated that human intestinal bacteria modulate *C. difficile* toxin A production in the intestine and that toxin A binds more on intestinal membranes isolated from axenic than conventional mice, indicating that indigenous micro-organisms play an important role in *C. difficile*'s pathogenesis. Clinical studies, testing nutritional approaches for treatment of *C. difficile*-induced colitis and diarrhoea, indicate that *Lactobacillus GG* improves the symptoms of colitis in hospitalised adults or infants. In a similar way the non-pathogenic yeast *Saccharomyces boulardii* has been shown to have positive effects in the prevention or treatment of *C. difficile*-induced colitis and diarrhoea in adults or infants. In addition RU 2168915 discloses the use of a meat product comprising predetermined ratios of beef, pork, blanched beef liver, squash or pumpkin, and butter as a curing or preventing food product against gastrointestinal disorders in children and weak people. All the above observations indicate that the field of nutritional intervention against *C. difficile* infection is still open.

SUMMARY OF THE INVENTION

The present invention relates to the use of an oral composition comprising peptones and/or meat extract to treat the effects of enterotoxins resulting from infection by pathogens. Such effects include failure of gut epithelial integrity due to the disassembly of actin filaments and the resulting disruption of tight junctions as well as diarrhoea resulting from toxin-induced secretion of intestinal fluid and other processes mediated by cyclooxygenase induction.

DETAILED DESCRIPTION OF THE INVENTION

In the present application, "oral composition" is intended to mean any ingestible composition, and may be a nutritional composition, a nutritional supplement, or a medicine. It may also be the adjuvant of a medicinal treatment, for example. It is intended to be used in humans, from infants or pre-termed infants to elderly people, suffering from the effects of enterotoxins resulting from infection by pathogens. It is also intended for pets, such as cats, dogs, fish, rabbits, mice, hamsters and the like, and more generally for any animal being bred by humans, such as horses, cows, fowl, sheep etc, suffering from the effects of enterotoxins resulting from infection by pathogens.

The term "meat extract" is intended to cover extracts of any meat, such as beef, pork, lamb, chicken and/or turkey, among others. It may also be from a mixture of the above-cited meats. In any event, it will provide at least nitrogen, amino acids, and carbon. An example of a suitable, commercially available meat extract for use in the present invention is BD Bacto Beef Extract supplied by Becton Dickinson and Company.

The term "yeast extract" may include the water-soluble portion of autolysed yeast, and preferably contains vitamin B complexes. It is also intended to cover an extract comprising both soluble and insoluble portions of autolysed bakers' yeast, and in this case it preferably further comprises riboflavin and panthotenic acid. However, in the preferred embodiment of the present invention, the "yeast extract" does not encompass the microorganism and does not comprise the enzymes produced by the microorganism. The yeast extract may be an extract from *Saccharomyces cerevisiae*. An example of a suitable, commercially available yeast extract for use in the present invention is BD Bacto Yeast Extract supplied by Becton Dickinson and Company The term "peptone" means any soluble mixture of products produced by the partial enzymatic or acid hydrolysis of proteinaceous material. The choice of protein starting material is not critical but casein, whey and meat proteins are preferred. Preferably, the molecular weights of the peptones are less than 3 kDa. An example of a suitable, commercially available peptone for use in the present invention is BD Bacto Peptone supplied by Becton Dickinson and Company Enterotoxins are bacterial exotoxins that have an action upon the intestinal mucosa. They may be produced within the intestine by pathogenic bacteria. Bacterial enterotoxins are potent mucosal immunogens that activate both mucosal and systemic immune responses and thus are the cause of various diseases, which include food poisoning, common diarrhoea, colitis, chronic inflammation and dysentery. Enterotoxins also lead to serious mucosal ulceration, haemorrhagic inflammatory exude or bloody diarrhoea. Toxin-induced diseases are often accompanied by abdominal cramps and rectal pain. Enterotoxins are the main stimulators of fluid secretion and intestinal inflammation. Their binding on the surface of epithelial cells leads to desegregation of filamentous actin and to increased permeability of the tight junctions as well as to activation of intracellular pathways and the subsequent synthesis and release of fluid secretion activators. Toxins also induce severe inflammation, usually characterized by transmigration of neutrophils in the mucosa and enterocyte necrosis, via the activation of sensory enteric nerves and the release of sensory neuropeptides, followed by release of cytokines and epithelial cell destruction.

Pathogenic bacteria may be part of the commensal microflora, that is may exist in the gut without harmful effect unless and until the balance of the microflora is disturbed as may happen, for example, during treatment with antibiotics, particularly broad spectrum antibiotics. In such circumstances, these "opportunistic pathogens" may grow rapidly, coming to dominate the intestinal microflora and produce toxins which cause enteritis. Examples of such bacteria include *Clostridium difficile* and *Clostridium perfringens* and the compositions of the invention are particularly well suited to treating the effects of toxins produced by such bacteria. It will be appreciated that the invention is thus particularly suitable for use in the treatment of nosocomial infections.

Examples of other enterotoxin-producing bacteria are *E. coli, Leishmania donovani, Vibrio cholera, Salmonella typh-* imurium, *Shingellae*, *Aeromonas hydrophila*, *Staphylococcus aureus*, or *enterotoxigenic Bacteroides fragilis* (ETBF).

*Clostridium difficile* infection is the main cause of colitis and diarrhoea in hospitalised patients, whose intestinal microbiota is altered due to antibiotics uptake. *C. difficile* causes enteritis by releasing two enterotoxins: toxin A and toxin B. Both toxins have a potent cytotoxic effect in humans but toxin A is the main stimulator of fluid secretion (therefore diarrhoea) and intestinal inflammation. Toxin A binds on the surface of epithelial cells and it is internalised into the cytoplasm in coated pits. Internalisation leads to disassembly of actin stress fibers, disruption of the actin-associated adhesion plaque, opening of the tight junctions, cell detachment and increased fluid secretion. These effects have been demonstrated in vitro on cultured human epithelial cell lines, such as the T84 colonic cell line, where addition of toxin A on the monolayer diminished the transepithelial resistance and increased the permeability of the monolayer. *C. difficile* enterotoxins in vivo have been shown to induce severe inflammation, characterized by transmigration of neutrophils in the mucosa and enterocyte necrosis, when guinea pig, rabbit or rat ileum have been exposed to toxin A. The mechanism leading to this acute inflammatory response appears to be the activation of sensory enteric nerves and the release of sensory neuropeptides. Recent studies also proposed that toxin A upregulates expression of COX-2 in the intestine.

One of the most common consequences of damages caused by gastro-enteric pathogens is diarrhoea. Diarrhoea is the result of increased secretions from the epithelial cells in the gut which may be induced by pathogenic bacteria (including enterotoxin-producing bacteria), parasites or viruses.

COX-2 is an enzyme catalyzing the synthesis of prostaglandins from arachidonic acid. Other known substrates for COX-2 include dihomo-gamma-linolenic acid (20:3n:6) and eicosapentaenoic acid (EPA, 20:5n-3) producing $PGE_1$, and $PGE_3$, respectively. The human COX-2 gene has been cloned and its genomic pattern and the responsiveness of its gene expression to different elements, such as cAMP, NF-κB and TGF-β, IL-1 or TNF-α has been described.

COX-2 is linked to numerous inflammations, including allergic reactions and gut inflammations. Among gut inflammations and disorders, wherein COX-2 activity is involved, are gastritis, inflammatory bowel disease, irritable bowel syndrome, or intestinal cancers.

Preferably, the peptones are given in form of an oral composition comprising, in volume, from 0.3 to 7% peptones. Suitable sources of peptones include whey protein and an extensively hydrolysed whey protein with an average peptide size not greater than five amino acids is particularly preferred although whey proteins with a degree of hydrolysis between 15 and 20% may also be used. Meat proteins are an alternative source of peptones and among meat proteins, beef proteins are preferred. Meat extract may be added, preferably in a quantity of from 0.3 to 7.0% by volume. In the preferred embodiment, the oral composition comprises (in volume) 1% of meat extract and 1% peptones. Further, the composition may include yeast extract, preferably at a concentration of 0.01 to 5% by volume.

The oral composition of the invention may take the form of various different food products. For example, it can be an infant formula powder when the target population is an infant population. It can also be a dehydrated food products, such as soups. It can further be an enteral composition or supplement formulas. When the individual suffering from an intestinal disorder is a pet, the oral composition can be any wet or dry pet food.

When the composition, according to the invention, is incorporated into a medicine, it can be incorporated together with any appropriate excipient to any medicinal form.

We have found that by ingesting meat extracts together or not with peptones, or peptones alone, individuals suffering from infection by pathogens as evidenced by intestinal disorders such as failure of gut epithelial integrity and diarrhoea have a normalised fluid secretion, a cellular structure less damaged, and a decreased inflammation compared to individuals having the same disorders, but a diet not supplemented with meat extracts nor peptones In the frame of the present invention, meat extracts and/or peptones may also be associated with yeast extract to obtain an improved effect on gut integrity into individuals subjected to gut upsets, damages and stresses.

EXAMPLES

The following examples are illustrative of some of the products falling within the scope of the present invention and methods of making the same. They are not to be considered in any way limitative of the invention. Changes and modifications can be made with respect to the invention. That is, the skilled person will recognise many variations in these examples to cover a wide range of formulas, ingredients, processing, and mixtures to rationally adjust the naturally occurring levels of the compounds of the invention for a variety of applications.

Example 1

Effect of the Composition on Tight Junctions and Actin Filaments

Material and Methods

The human colonic cell line T84 (ATCC, CCL-248) was cultured in DMEM:F12 1:1 supplemented with 20% FBS (Foetal Bovine Serum), 2 mM glutamine and 100 U/ml penicillin-streptomycin. Human primary skin fibroblasts were cultured in DMEM supplemented with 10% FBS and 100 U/ml penicillin-streptomycin.

T84 monolayers were seeded in 6-well inserts plates at $0.5 \times 10^6$ cells/insert and cultured during 3 weeks. The basal value of the TEER (Transepithelial Electrical resistance) was measured and culture medium was replaced by 20% of a solution of de Man-Rogosa-Sharpe growth medium (a solution containing 1% beef extract, 1% meat peptones and 0.5% yeast extract in PBS hereinafter referred to as "MRS"). After 1 h at 37° C., *C. difficile* toxin A was added in the apical side of the monolayers at a final concentration of 100 ng/ml and the TEER were further measured after 1, 2, 4, 6 and 24 h at 37° C. Control monolayers were exposed to cultured media only. For each condition triplicate inserts were used. At each time point, 1 ml apical and 1 ml basolateral medium was collected and cell viability was evaluated by measuring the LDH release using the Cytotoxicity Detection Kit according to the manufacturers' instructions.

T84 cells or human primary fibroblasts ($2 \times 10^5$/chamber) were seeded on 4-chamber glass slides, grown as described previously and incubated with a 20% solution of MRS for 1 h before addition of toxin A at a final concentration of 500 ng/ml. After 6 h, cells were washed with PBS, fixed with 3.7% paraformaldehyde, washed twice with PBS, permeabilized for 5 min at −20° C. with acetone and treated with PBS-1% BSA (Bovine Serum Albumin) to reduce non-specific labelling. Actin desegregation and cell rounding were assessed by fluorescent microscopy after labelling with 200 U/ml rhodamine-labelled phallotoxin.

Results

Toxin A affects tight junctions of epithelial cells, an effect which is measured by the decrease of the transepithelial electrical resistance (TEER) of epithelial monolayers. To assess whether MRS could counteract the virulence of toxin A, T84 monolayers were exposed to toxin A in the presence or absence of the composition and TEER were measured. Addition of 100 ng/ml toxin A to T84 monolayers resulted in a 3-fold reduction of TEER control values after 6 h of incubation (309±8 vs. 985±49 $\Omega cm^2$). Addition of a 20% solution of MRS together with toxin A, prevented the TEER decrease (1403±95 vs. 309±8 $\Omega cm^2$), while it did not alter the basal TEER values of T84 cells (1217±277 $\Omega cm^2$ vs. 985±49 $\Omega cm^2$). No modifications in cell viability were observed, indicating that toxin A does not induce cell death during the 6 h period. The above results demonstrate that a mixture of peptones, meat extract and yeast extract could counteract toxin A and protect T84 monolayers from toxin A-induced TEER decrease.

To determine whether the protective effect of MRS against toxin A-induced TEER decrease was correlated with alteration of the cytoskeleton leading to cell rounding, T84 cells were treated with toxin A alone or in combination with a 20% solution of MRS and cytoskeletal actin was analysed by immunocytochemistry. Addition of 500 ng/ml toxin A induced T84 cell rounding, which is evidenced by the bee nest appearance of the cell monolayer due to actin desegregation, and packaging. Addition of a 20% solution of MRS in combination with toxin A partially prevented actin desegregation and subsequent cell rounding induced by toxin A, while it did not influence the cytoskeleton of the cells when added alone. These effects were hardly visible due to the spatial configuration of the T84 monolayer. To render the interpretation easier, experiments were repeated using primary human skin fibroblasts, which form a planar monolayer. After 6 h in the presence of toxin A, all fibroblasts presented a round appearance indicating a complete cytoskeletal disruption. Addition of a 20% solution of MRS in combination with toxin A partially prevented actin desegregation and cell rounding. The shape of fibroblasts treated with toxin A and 20% of the composition was comparable but not identical to the shape of control fibroblasts or of fibroblasts treated with the combination alone. Thus MRS could counteract toxin A, partially preventing cytoskeletal alterations and subsequent cell rounding, due to actin desegregation.

These experiments were then repeated replacing the 20% MRS solution by the following:
20% solution of a 1% solution of beef peptones
20% solution of a 1% solution of beef extract
20% solution of a 0.5% solution of yeast extract
1% of a solution containing extensively hydrolysed whey peptides (average peptide size less than about 5 amino acids) 10% of a solution containing extensively hydrolysed whey peptides (average peptide size not greater than 5 amino acids)

Similar results were obtained as with the 20% MRS solution.

Discussion

The mechanisms of the protective action observed here are not clearly elucidated and probably are diverse. Toxin A induces polymerisation of actin filaments, leading to desegregation of cytoskeletal actin. Actin disruption is the cause of cell rounding, observed in vitro, and increased permeability of the tight junctions. The toxin A effect on actin is due to its glucotransferase activity against the Rho family of proteins. Toxin A is able to enzymaticaly transfer a glucosyl residue from UDP glucose to threonine 37 of Rho, Rac and Cdc-42, leading to disassembly of actin stress fibers, disruption of the actin-associated adhesion plaque, opening of the tight junctions, cell detachment and increased fluid secretion. Those effects have been demonstrated in vitro on T84 cells, where addition of toxin A on the monolayer diminished the transepithelial resistance and increased the permeability of the monolayer, due to modifications of the Rho proteins in the epithelial cells. Therefore we believe that peptones, yeast extract, and beef extract interfere with the signalling pathway of the Rho proteins, inhibiting the effects of toxin A. Although not wishing to be bound by theory, this interference could be up-stream or down-stream of the transfer of the glucosyl residue to Rho proteins.

Example 2

Effect of the Composition on Damages Caused by Enterotoxin-Producing Gastro-Enteric Pathogens Material and Methods Six weeks old male mice were treated ad libitum with 60 mg/L gentamicin, 250 mg/L vancomycin, 300 mg/L amoxicillin and 10 mg/L amphotericin for a week in order to eliminate the intestinal microbiota. Mice were then divided into three groups: i) a control group; ii) a group receiving ad libitum a 20% solution of MRS in the drinking water, for a week; and iii) a group that was gavaged twice with 500 µl the composition at two day interval. The day after the end of treatments, animals were anaesthetized with 30 mg/kg of body weight sodium pentobarbital and placed on a warm blanket (37° C.), under 0.8-3% isofluoran anaesthesia for the whole duration of the operation. The abdomen was opened by a midline incision and the distal jejunum was exposed. Two 5 cm jejunal segments were doubly ligated at each end with surgical thread to form two intestinal loops with a 2 cm interval between them. One loop was injected with 600 µl PBS as a control and the other with 600 µl PBS containing 20 µg toxin A. The intestinal loop was then returned to the abdominal cavity and the incision was sutured closed. Mice were allowed to recover and they were followed continously. Animals were euthanised after 4 h, the loops were isolated and their weight to length ratio (in mg/cm) was recorded to estimate fluid secretion. Loops were then washed twice with ice cold PBS, dipped in RNAlater™, flashed frozen in liquid nitrogen and stored at −80° C.

Results

*C. difficile* infection, leading to diarrhoea and colitis, develops mostly in hospitals and elderly people's homes striking patients who take antibiotics and thus their intestinal microbiota is altered. To assess whether the composition of the invention and its components can counteract toxin A effects in vivo, a mouse model was used. To mimic the conditions that trigger *C. difficile* infection in humans, mice were treated for a week with antibiotics aimed to alter their intestinal microbiota. One day after the end of antibiotic treatment, a group of mice were given the 20% solution of MRS ad libitum for one week. At the end of this period, intestinal loops were formed and injected with PBS or 20 µg toxin A. After 4 h incubation, loops from control mice exhibited an increased fluid secretion when injected with toxin A compared to PBS injected loops (121.9±31.7 vs. 64.6±13.5 mg/cm). In contrast, in mice receiving the MRS for one week, no differences in fluid secretion were observed in loops injected with toxin A or PBS (73.6±8.3 vs. 66.8±10.8 mg/cm). Similar results were obtained when mice were given by gavage two doses of 500

µl of the 20% MRS solution. These results show that treatment with peptones, meat extract and yeast extract can prevent the adverse effect of toxin A in subjects exhibiting an impairment of the intestinal microbiota.

To determine whether the composition exerts its protective action by direct inactivation of toxin A, the 20% MRS solution, or PBS as a control, were mixed with toxin A 1 h before injecting the mixture in the intestinal loops of mice, treated for a week with antibiotics. There was not a significant difference recorded between control (PBS) and the MRS-injected loops at the level of toxin A-induced fluid secretion. This result indicates that the composition does not counteract the effects of toxin A via direct binding and inactivation of the toxin, which could lead to either toxin-cleavage or masking of the toxin-binding epitopes.

Discussion

The MRS composition protected the mice from intestinal fluid secretion induced by toxin A. Although not wishing to be bound by theory, we believe that the protective action of peptone, beef extract and yeast extract are not due to an enzymatic activity, which cleaves toxin A for two main reasons: i) The solutions used were always autoclaved, which would lead to disactivation of any enzymes, such as proteases, contained in the solution and ii) The composition mixed and incubated with toxin A before being injected in the intestinal loops of mice, could not inhibit intestinal fluid secretion. Therefore we do believe that the protective activity of peptone, yeast extract and beef extract is due to the presence of free molecules in the solution (e.g. aminoacids or peptides), which could bind on the toxin A receptor on the intestinal epithelial cells and prevent binding of toxin A and the activation of the signalling pathways involved.

Example 3

Effect of the Composition on the Expression of COX-2

Materials and Methods

The same procedure described in example 2 was used. The RNA was extracted from mouse intestinal loops, and COX-2 mRNA expression was assessed by RT-PCR. Total RNA (1 µg) was reverse transcribed with 200 U of Superscript II® enzyme. A 400 bp fragment of mouse COX-2 was amplified by PCR using 5'-CACAGTACACTACATCCTGACC-3' as sense and 5'-TCCTCGCTTCTGATTCTGTCTTG-3' as antisense primers. A 700 bp fragment of β-actin, used as an internal control, was amplified from the same RT mix with the 5'-ATGAGGTAGTCTGTCAGGT-3' as sense and 5'-ATGGATGACGATATCGCT-3' as antisense primers. To exclude DNA contamination, PCR was performed directly on RNA samples. PCR products were loaded on 1% agarose gel, photographed, and pictures used for densitometrical quantification of band intensities. Normalization was performed against the expression of the internal control β-actin: the ratios of the COX-2 and the corresponding β-actin mRNA signals were determined and expressed relative to that of the "not-treated sample" (given water and injected with PBS) to which an arbitrary score of 1 was assigned.

Results

To determine whether COX-2, known to be involved in toxin A-mediated fluid secretion, is also implicated in the composition's protective effect, COX-2 MRNA expression was assessed by RT-PCR. Changes in COX-2 expression due to different treatments were expressed relative to β-actin. Injection of 20 µg toxin A in the intestinal loops of control mice resulted in a 3.6-fold increase of COX-2 mRNA expression. Treatment of mice for one week with the composition resulted in a 2-fold reduction of the COX-2 increase mediated by toxin A. Intestinal COX-2 expression induced by toxin A was completely normalised to basal levels in mice under peptone or beef extract treatments while it was decreased by 2.3-fold under yeast extract treatment. Neither the composition nor its components significantly modified the basal levels of COX-2 mRNA expression. When given by gavage, the composition or its components were also able to counteract the increase in COX-2 mRNA induced by toxin A.

Discussion

When toxin A binds on the epithelial cells it is shown to induce inflammation, including neutrophil migration and enterocyte necrosis and destruction of the villus. These effects are mediated by the release of sensory neuropeptides, such as substance P and calcitonin gene-related peptide, following the activation of sensory enteric nerves. In addition expression on the intestinal epithelium of NK-1R the receptor for SP significantly increases both in animals and in humans infected with *C. difficile*. Recent studies also proposed that toxin A of *C. difficile* upregulates expression of COX-2 in the intestine. COX-2 is the inducible isoform of the cyclooxygenase enzyme, which mediates synthesis of prostaglandin E2 (PGE2) an agent known to increase intestinal fluid secretion, which leads to diarrhoea. Although not wishing to be bound by theory, we believe that peptone, yeast extract and beef extract inhibit any of these pathways counteracting toxin A. Our results indicate that peptone, yeast extract or beef extract inhibit intestinal, toxin-mediated, COX-2 induction. This could be due to inhibition of toxin A-mediated signalling, which leads to COX-2 activation if our solutions inhibit or reduce binding of the toxin on its intestinal receptor.

The invention claimed is:

1. A method for treating the effects of infection by enterotoxin-producing pathogens, the method comprising administering to a human or animal in need of same an oral composition comprising from about 0.3% to about 7% by volume of a meat peptone and about 0.3% to about 7% by volume of a meat extract.

2. The method of claim 1, wherein the effects include failure of gut epithelial integrity, diarrhoea and other COX-2 mediated effects.

3. The method of claim 1, wherein the pathogen is *Clostridium difficle, Clostridium perfringens, E. coli, Leishmania donovani, Vibrio cholera, Salmonella typhimurium, Shingellae, Aeromonas hydrophila, Staphylococcus aureus*, and/or enterotoxigenic *Bacteroides fragilis*.

4. The method of claim 1, wherein the oral composition further comprises a yeast extract.

5. The method of claim 1, wherein the oral composition is an adjuvant to a medicinal treatment.

6. The method of claim 1, wherein the oral composition is an infant formula or an enteral composition.

7. A method for treating the effects of infection by enterotoxin-producing pathogens, the method comprising administering to a human or animal in need of same an oral composition comprising from about 0.3% to about 7% by volume of a meat peptone, about 0.3% to about 7% by volume of a meat extract, and from 0.01 to 5% by volume of a yeast extract.

8. The method of claim 7, wherein the oral composition is an adjuvant to a medicinal treatment.

9. The method of claim 7, wherein the oral composition is an infant formula or an enteral composition.

\* \* \* \* \*